United States Patent
St. Clair et al.

(10) Patent No.: US 6,562,990 B1
(45) Date of Patent: May 13, 2003

(54) TITANIUM CHELATES AND PROCESSES THEREFOR

(75) Inventors: Jerry Dale St. Clair, Wallingford, PA (US); Norman A. Carlson, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/189,076

(22) Filed: Jul. 3, 2002

(51) Int. Cl.$^7$ .................................................. C07F 7/20
(52) U.S. Cl. ........................................... 556/40; 556/54
(58) Field of Search ..................... 556/40, 54

(56) References Cited

U.S. PATENT DOCUMENTS

| | | | |
|---|---|---|---|
| 4,551,544 A | 11/1985 | Robbins | 556/40 |
| 4,647,680 A | 3/1987 | Barfurth et al. | 556/40 |
| 4,924,016 A | 5/1990 | Barfurth et al. | 556/40 |
| 5,349,073 A | 9/1994 | Horn et al. | 556/54 |
| 5,767,302 A | 6/1998 | Ogi et al. | 556/54 |

FOREIGN PATENT DOCUMENTS

| | | |
|---|---|---|
| JP | 5-271253 A | 10/1993 |
| JP | 2001-172219 A | 6/2001 |
| WO | WO 84 03042 A | 8/1984 |

*Primary Examiner*—Porfirio Nazario-Gonzalez

(57) ABSTRACT

A composition and processes for producing the composition are provided. The composition comprises titanium chelates having the formulae of $TiX_m(OR)_{4-m}$, $TiX_m(OR)_{(4-m)/2}(OR^1)_{(4-m)/2}$, and $TiX_m(OR^1)_{4-m}$ in which X is a radical derived from a chelating agent such as, for example, a diketone, a diester, a ketoester, or combinations of two or more thereof; m is a number from about 1.5 to about 2.5; each R and $R^1$ is independently an alkyl group containing from 1 to about 10 carbon atoms per radical; and $R^1$ differs from R. The process can comprise contacting at least one tetraalkyl titanates with a chelating agent to produce a product mixture comprising a titanium chelate and an alcohol, substantially removing the alcohol to produce an alcohol-reduced titanium chelate, optionally contacting the alcohol-reduced titanium chelate with a second, and further optionally reducing the alcohol content of the titanium.

21 Claims, No Drawings

TITANIUM CHELATES AND PROCESSES THEREFOR

FIELD OF THE INVENTION

This invention relates to a composition and processes therefor in which the composition comprises chelates of titanium alkoxides having low freezing points.

BACKGROUND OF THE INVENTION

Titanium chelates have a number of industrial uses. They are valuable in a variety of applications such as catalysis, corrosion inhibition, crosslinking and other applications. Their formula can be depicted as $(RO)_2TiX_2$ where X is derived from a chelating agent such as, for example, 2,4-pentanedione and R is a straight or branched alkyl group. They can be made by reacting a titanium orthoester of the formula $Ti(OR)_4$ such as, for example, tetraisopropyl titanate (also known as tetraisopropoxy titanium) with approximately two equivalents of chelating agent such as, for example, 2,4-pentanedione (also known as acetyl acetone) accompanied by the release of two equivalents of the alcohol of the formula ROH.

In such titanium chelates made from a single alcohol, the compounds may have high freezing points and be difficult to handle. Some may initially be a liquid, even remaining as a liquid even after having been supercooled to some considerable extent, but then freeze spontaneously, especially in the presence of a nucleating agent such as dust or part of the reaction product in crystal form. To prevent this, these titanium chelates may be left in the reaction solution in which they were formed, that is, still containing the byproduct alcohol rather than removing it. However this is a disadvantage when the solutions are used in industry because of the resulting low flash point of the solution and the creation of solvent pollution/disposal problems. Preferably, the titanium chelate product is essentially alcohol-free.

Mixed alcohol chelates generally have lower freezing points than chelates of a single alcohol, and are thus liquid at temperatures of typical use even with all byproduct alcohol removed. Mixed chelates can be produced from a mixture of titanium orthoesters with a chelating agent. However, when such alcohols are removed from their mixtures, it is often difficult to control the ratio of alkoxides in the resulting product. This is due to distinct alcohols having different boiling points and being retained to differing and variable extents during their removal from the reaction mass, resulting in often unpredictable and variable product compositions.

U.S. Pat. No. 4,551,544 discloses a reaction product of a titanate $(OR^1)_4Ti$, 2,4-pentanedione, and either another titanate $(OR^2)_4Ti$ or an alcohol $R^3OH$. U.S. Pat. No. 5,349,073 discloses admixing diisopropoxy titanium bis(acetylacetonate) with a dialkoxy titanium bis(acetylacetonate) to produce isopropoxyalkoxy bis(acetylacetonate) titanium.

However, the alcohol content in the known products is higher than desired. Additionally, the known process requires multiple steps. Also, many of the component chelates can freeze at typical ambient temperatures making the storage more time consuming and can require exposing the material to extended heating in order to thaw it for recharging. Such extended heating can lead to excessive color development in the products.

Therefore, a new product and a process therefor are needed in which the product comprises mixed titanium chelates, is essentially or substantially alcohol-free, and has constant and predictable composition.

SUMMARY OF THE INVENTION

According to a first embodiment of the invention, a substantially alcohol-free composition is provided, which comprises (A) $TiX_m(OR)_{4-m}$, (B) $TiX_m(OR)_{(4-m)/2}(OR^1)_{(4-m)/2}$, and (C) $TiX_m(OR^1)_{4-m}$ wherein X is a radical derived from a chelating agent comprising an organic 1,3-dicarbonyl compound; m is a number from about 1.5 to about 2.5; each R and $R^1$ is independently a hydrocarbyl radical containing from 1 to about 10 carbon atoms per radical; and $R^1$ differs from R.

According to a second embodiment of the invention, a process comprises (1) contacting a tetraalkyl titanate with a chelating agent to produce a product mixture comprising a titanium chelate and an alcohol; (2) optionally substantially removing the alcohol whereby an alcohol-reduced titanium chelate is produced; (3) contacting the product mixture or alcohol-reduced titanium chelate with a second alcohol to produce another alcohol-reduced titanium chelate; and optionally (4) reducing the alcohol content of the another alcohol-reduced titanium chelate to produce a substantially alcohol-free titanium chelate wherein the second alcohol is less volatile than the alcohol derived from the tetraalkyl titanate.

Also according to a third embodiment of the d invention, a process comprises (1) contacting a mixture comprising a tetraalkyl titanate and a second tetraalkyl titanate with a chelating agent to produce a product mixture comprising a titanium chelate and a mixture of alcohols derived from the tetraalkyl titanate and second tetraalkyl titanate; (2) substantially removing the mixture of alcohols to produce an alcohol-reduced titanium chelate; and optionally (3) reducing the alcohol content of the alcohol-free reduced titanium chelate to produce a substantially alcohol-free titanium chelate.

According to a fourth embodiment of the invention, a process comprises (1) contacting a single-alcohol titanium chelate with an alcohol, a second single-alcohol titanium chelate, or both to form a desired statistical mixture of (A), (B) and (C) disclosed above in the first embodiment of the invention; (2) substantially removing the mixture of alcohols to produce an alcohol-reduced titanium chelate; and optionally (3) reducing the alcohol content of the alcohol-reduced titanium chelate to produce a substantially alcohol-free titanium chelate.

DETAILED DESCRIPTION OF THE INVENTION

The term "less volatile" refers to the boiling point of an alcohol being at least about 20° C. higher than that of another alcohol, and the term "similar boiling points" refers to boiling points of alcohols that are within about 5° C.

According to the first embodiment, X is a radical derived from a chelating agent. A preferred chelating agent is an organic 1,3-dicarbonyl compound such as a diketone, a diester, a ketoester, and combinations of two or more thereof. A radical derived from any 1,3-diketone can be used. The preferred diketones include, but are not limited to, 2,4-pentanedione, 1,4-hexanedione, 1,3-pentanedione, 2,4-hexanedione, dipivaloyl methane, or combinations of two or more thereof.

Also, a radical derived from any 1,3-diester can be used. The preferred diesters include, but are not limited to, dimethyl malonate, diethyl malonate, or combinations thereof.

Similarly, a radical derived from any 1,3-ketoester can be used. The preferred ketoester include, but are not limited to, methyl acetoacetate, ethyl acetoacetate, isopropyl acetoacetate, butyl acetoacetate, and combinations of two or more thereof.

The most preferred chelating agent is 2,4-pentanedione, ethyl acetoacetate, or combinations thereof.

The preferred m is a number in the range from about 1.5 to about 2.5, preferably from 1.65 to about 2.2, more preferably from 1.8 to about 2.1, and most preferably about 1.9 to about 2. Those skilled in the art can recognize that in cases where m is not 2.0, structures A, B, and C will not have integral numbers of groups and actually are abbreviated shorthand representations of the actual components. In these cases, A, B, and C represent the average compositions of individual components having integral numbers of groups totaling 4 in number for all individual components.

The preferred R or $R^1$ is hydrocarbyl radical having 1 to about 10 carbon atoms per radical including, but not limited to alkyl radical, cycloalkyl radical, alkylenyl radical, aryl radical, alkaryl radical, aralkyl radical, or combinations of two or more thereof. Examples of suitable radicals include, but are not limited to methyl, ethyl, propopyl, isopropyl, butyl, isobutyl, pentyl, sec-butyl, tert-butyl, and combinations of two or more thereof. However, $R^1$ is different from R in the same titanium chelate complex.

Examples of mixed titanium chelates include, but are not limited to,
Ti(CH$_3$C(O)CHC(O)CH$_3$)$_{1.95}$(OCH(CH$_3$)$_2$)$_{2.05}$,
Ti(CH$_3$C(O)CHC(O)CH$_3$)$_{1.95}$(OCH(CH$_3$)$_2$)$_{1.025}$ (OCH$_2$CH$_2$CH$_2$CH$_3$)$_{1.025}$,
Ti(CH$_3$C(O)CHC(O)CH$_3$)$_{1.95}$(OCH$_2$CH$_2$CH$_2$CH$_3$)$_{2.05}$;
Ti(CH$_3$C(O)CHC(O)CH$_3$)$_{1.95}$(OCH(CH$_3$)$_2$)$_{2.05}$,
Ti(CH$_3$C(O)CHC(O)CH$_3$)$_{1.95}$(OCH(CH$_3$)$_2$)$_{1.025}$ (OCH$_2$CH$_3$)$_{1.025}$,
Ti(CH$_3$C(O)CHC(O)CH$_3$)$_{1.95}$(OCH(CH$_3$)$_2$)$_{2.05}$;
Ti(OC(CH$_3$)CHC(O)CH$_3$)$_{1.95}$(OCH(CH$_3$)$_2$)$_{2.05}$,
Ti(OC(CH$_3$)CHC(O)CH$_3$)$_{1.95}$(OCH(CH$_3$)$_2$)$_{1.025}$ (OCH$_2$CH$_2$CH$_2$CH$_3$)$_{1.025}$,
Ti(OC(CH$_3$)CHC(O)CH$_3$)$_{1.95}$(OCH$_2$CH$_2$CH$_2$CH$_3$)$_{2.05}$;
Ti(OC(CH$_3$)CHC(O)CH$_3$)$_{1.95}$(OCH(CH$_3$)$_2$)$_{2.05}$,
Ti(OC(CH$_3$)CHC(O)CH$_3$)$_{1.95}$(OCH(CH$_3$)$_2$)$_{1.025}$ (OCH$_2$CH$_3$)$_{1.025}$,
Ti(OC(CH$_3$)CHC(O)CH$_3$)$_{1.95}$(OCH$_2$CH$_3$)$_{2.05}$, and combinations of two or more thereof.

The composition can be characterized as having a low freezing point. The term "low" refers to a freezing point lower than about 30° C., preferably about 20° C., and most preferably 0° C.

The composition can also be characterized as being essentially or substantially alcohol-free. That is, the alcohol content in the composition is about 5% or lower, preferably about 3% or lower, and most preferably about 2% or lower, by weight.

The composition of the titanium chelates of the present invention can be characterized as follows by high resolution nuclear magnetic resonance (NMR) spectroscopy following the method described below. It is to be understood that one skilled in the art may develop other methods of analysis that give an equivalent separation of the titanium chelate species involved, and that these are all within the scope of the inventive process.

A small portion of the sample is dissolved in deuterated benzene (or other suitable anhydrous NMR solvent) at a concentration typically employed for proton and carbon NMR analysis. The sample is scanned in both the proton ($^1$H) and carbon ($^{13}$C) frequency regions to generate proton and carbon spectra of the sample. In order to resolve the peaks for the individual components of the chelate mixtures, a high resolution NMR apparatus is employed. Any of the typical high field NMR instruments in common usage should generate acceptable spectra. The NMR analyses cited in the examples were performed on a Bruker NMR using the following conditions and parameters:

Carbon ($^{13}$C) NMR spectra:
  Frequency: 125.8 MHz
  Acquisitions: 512
  Pulse Width: 7.5 μsec
  Recycle Delay: 1 sec
  Sweep Width: 39682.5
  Acquisition time: 1.652 sec
  Offset Frequency: 15928.7
  Decoupling Mode: full $^1$H decoupling Proton ($^1$H) NMR spectra:
  Frequency: 500.3 MHz
  Acquisitions: 8
  Pulse Width: 11.5 μsec
  Recycle Delay: 30 sec
  Sweep Width: 10330.6
  Acquisition time: 6.344 sec
  Offset Frequency: 3066.2

The analyses are illustrated in the EXAMPLES section.

Wishing not to be bound by theory, it is believed that the composition disclosed herein is a statistical mixture of titanium chelates arising from free alcohol exchange. The composition can be analyzed in such a way as to distinguish between the individual chelates thereby making an essentially alcohol-free and uniform. By a statistical mixture is meant that the ratio of the above compounds A, B and C in the mixture is given by a:b:c where $$a = \text{relative moles of titanium chelate } A = \frac{r1^2}{(r1+r2)^2}$$

$$b = \text{relative moles of titanium chelate } B = \frac{2r1r2}{(r1+r2)^2}$$

$$c = \text{relative moles of titanium chelate } C = \frac{r2^2}{(r1+r2)^2}$$

and where r1=total moles of (OR) in the mixture, and r2=total moles of (OR') in the mixture. The ratio of r1 to r2 can be in the range of from about 0.5:1 to about 2:1 and preferably about 1:1. That is, the molar ratio of a:b can be in the range of from about 0.25:1 to about 1:1 and the molar ratio of c:b can be in the range of from about 0.25:1 to about 1:1. If the ratio of r1 to r2 is about 1:1, the percentage of a, b, and c are about 25%, 50%, and 25%, respectively.

The composition of the invention can be produced by any methods known to one skilled in the art. However, it is preferred it be produced by the processes disclosed in the invention.

According to the second embodiment of the invention, the tetraalkyl titanate, which can also be referred to by one skilled in the art as titanium tetraalkoxide, can have the formula of Ti(OR)$_4$ where each R is individually a hydrocarbyl radical, as disclosed above, and can contain from 1 to about 10, preferably 1 to about 8, and most preferably 2 to 5 carbon atoms per radical and each R can be the same or different. Suitable tetraalkyl titanates include, but are not limited to, tetraethyl titanate, tetrapropyl titanate, tetraisopropyl titanate, tetrabutyl titanate, tetraisobutyl titanate, tetra-tert-butyl titanate, tetrahexyl titanate, and combinations of two or more thereof. The preferred tetraalkyl titanate is tetraethyl titanate, tetraisopropyl titanate, or combinations thereof.

The chelating agent is the same as that disclosed in the first embodiment of the invention.

The product mixture comprises a titanium chelate and an alcohol. The titanium chelate comprises at least one compound selected from (A) and (C) disclosed in the first embodiment of the invention.

The alcohol produced is derived from the tetralkyl titanate and therefore has the same carbon number as the titanate. For example, if tetraethyl titanate is employed, the alcohol or third alcohol is ethanol and if tetraisopropyl titanate is used, it is isopropanol.

The second alcohol can be an alcohol depending on the type of tetraalkyl titanate used. The second alcohol can be any alcohol so long as the alcohol is less volatile than the alcohol derived from the tetraalkyl titanate and can produce a composition having the characteristics disclosed in the first embodiment of the invention. It can have the formula of $R^1OH$ such as propanol, isopropanol, butanol, isobutanol, t-butanol, pentanol, isopentanol, hexanol, heptanol, or combinations of two or more thereof.

The molar ratio of tetraalkyl titanate to the chelating agent can be any ratio so long as the ratio can produce a composition having the characteristics disclosed in the first embodiment of the invention. Generally, the ratio is the one that produce mixed chelated having the numbers of m disclosed above.

The molar ratio of the second alcohol, to the tetraalkyl titanate can be any ratio so long as the ratio can produce a composition having the characteristics disclosed in the first embodiment of the invention.

Generally, the ratio can be in the range of from about 0.5:1 to about 4:1 preferably about 0.7:1 to about 1.2:1, and most preferably about 1:1.

The process can be carried out under any suitable condition effective to produce a product mixture comprising the composition disclosed in the first embodiment of the invention. A suitable condition for producing a titanium chelate from a tetraalkyl titanate can include a temperature below about 80, preferably below about 70, and most preferably below about 65° C. under any pressure that can accommodate the temperature, preferably atmospheric pressure, for a period in the range of from about 0.1 to about 100, preferably about 0.5 to about 50, more preferably about 0.5 to about 30, and most preferably about 0.5 to about 15 minutes.

Removal of the alcohol liberated can be carried out by any means known to one skilled in the art to produce a second product mixture comprising an alcohol-reduced titanium chelate. For example, it can be carried out by distillation under a reduced pressure in the range of from about 1–200 mm Hg (0.13 to 26.7 kPa) for limited color formation and best alcohol removal. It can also be carried out by distillation at atmospheric pressure.

The another alcohol-reduced titanium chelate, or second product mixture produced from the alcohol-reduced titanium chelate and the second alcohol, can comprise a mixed titanium chelates comprising the radicals derived from the chelating agent and the second alcohol. This mixture can optionally be brought back to atmospheric pressure and, for example, further mixed such as by mechanical agitation at about 50 to about 80° C. for about 1 minute or until the components have sufficient time to react to liberate more alcohol which can be removed as disclosed above.

Thereafter, the another alcohol-reduced titanium chelate can be further "polished" or "reduced" by contacting it with an inert fluid. The reduction can be carried out (1) by contacting said substantially alcohol-free titanium chelate with an inert fluid, (2) under a reduced pressure, or (3) combination of (1) and (2). An inert fluid is one that does not react with a titanium chelate and can be liquid, gas, or combinations thereof. Examples of inert fluids include, but are not limited to nitrogen, carbon dioxide, and combinations thereof. Other methods such as, for example, vacuum, purging with nitrogen, vacuum cycling, or combinations of these and other methods that are apparent to those skilled in the art can also be used.

According to the third embodiment of the invention, the tetraalkyl titanate is the same as that disclosed above. The second tetraalkyl titanate can have the formula of $Ti(OR^1)_4$ where $R^1$ is the same as that disclosed above. Example of suitable second tetraalkyl titanate can be the same as those illustrated above for the tetraalkyl titanate. However, when simultaneously used with the tetraalkyl titanate, the $R^1$ in the second tetraalkyl titanate cannot be the same as R. The suitable chelating agents can also be the same as those disclosed above.

The molar ratio of the tetraalkyl titanate to second tetraalkyl titanate can be any ratios depending on the desired characteristics of the final product. For example, the ratio can be about 1:1. The conditions for contacting the mixture of tetraalkyl titanate and second tetraalkyl titanate with the chelating agent can be the same as the contacting of the tetraalkyl titanate with the chelating agent disclosed in the first embodiment of the invention. The alcohols generated correspond to the tetraalkyl titanate and the second tetraalkyl titanate used and can be removed by the process disclosed above in the second embodiment of the invention. Similarly, the alcohol-reduced titanium chelate can also be similarly "polished" as disclosed above.

According to the fourth embodiment of the invention, a process for producing an essentially alcohol-free statistical mixture of compounds of the formulas (A) $TiX_m(OR)_{4-m}$, (B) $TiX_m(OR)_{(4-m)/2}(OR^1)_{(4-m/2)}$, and (C) $TiX_m(OR^1)_{4-m}$ comprises contacting a compound of formula (A) with at least sufficient amounts of an alcohol $R^1OH$ to form the desired statistical mixture of (A), (B) and (C), and removing the free alcohol from the mixture, using the process disclosed above, to a level of 2.0% by weight or lower in a manner that provides an essentially constant proportion of R to $R^1$ by weight. Compound (A) can be produced by contacting a tetraalkyl titanate with a chelating agent as disclosed in the second and third embodiments of the invention. Contacting a compound of formula (A) with $R^1OH$ can be carried out under a suitable condition disclosed above in the second embodiment of the invention. Preferably, the product mixture is analyzed by a method that distinguishes between (A), (B) and (C). This is particularly desirable in initial production until satisfactory controls of product quality are established. Preferably the analysis is carried out by high resolution nuclear magnetic resonance.

Optionally, the essentially constant proportion of R to $R^1$ by weight can be obtained by careful control of the distillation temperature, pressure. reflux ratio and other variables, once the product composition is established and confirmed by an analytical method that distinguishes between (A), (B) and (C).

The processes of the invention requires a one pot reaction and no blending operation, resulting in reduced cycle time, increased productivity, and reduced cost due to elimination of intermediate storage and mixing steps.

The process can be depicted as $Ti(OR)_4 + Ti(OR^1)_4 + 4X \rightarrow 2TiX_2(OR)(OR^1) + 2ROH + 2R^1OH$ for the case in which m=2 and $TiX_2(OR)(OR^1)$ is a shorthand representation of the previously described statistical mixture.

EXAMPLES

The following examples are intended to illustrate the invention and should not be interpreted to limit the scope of the invention.

Example 1

Similar Boiling Points

The apparatus consisted of a 2 l flask (pot) equipped with magnetic stirring, addition funnel, and nitrogen inlet. The equipment was dried and inerted with nitrogen. To the flask was charged 278.3 g (0.9791 mol) of tetraisopropyl titanate and 340.0 g (1.4344 mol) of a mixture containing 81.0% (w/w) tetraethyl titanate and 19.0% (w/w) tetraisopropyl titanate. To the addition funnel was charged 471.2 g (4.7064 mol) of acetyl acetone. The system was inerted with nitrogen and stirring was started.

The acetyl acetone was added to the titanate dropwise (cooling may be applied if desired to remove reaction heat). After all of the acetyl acetone was added, the mixture was stirred for 15 minutes.

The addition funnel was replaced with a vacuum distillation head. The liberated isopropyl and ethyl alcohols were removed by vacuum distillation at 200 mbar (20 kPa), keeping the pot temperature below 70° C. The product obtained in this manner contained several percent residual free alcohol, which was reduced further by stripping at 70° C. and 5–15 mbar (0.5–1.5 kPa) pressure.

High resolution $^1$H- and $^{13}$C-NMR showed that the final product contained 24 molar % of $Ti(C_5H_7O_2)_2(OC_3H_7)_2$, 49 molar % of $Ti(C_5H_7O_2)_2(OC_3H_7)(OC_2H_5)$, and 27 molar % of $Ti(C_5H_7O_2)_2(OC_2H_5)_2$. These ratios exclude free alcohol, which was found to be 0.7 weight % isopropyl alcohol and 0.3 weight % ethyl alcohol. The overall ratio of bound isopropoxy to ethoxy groups was 1.0 versus a target of 1.0.

Example 2

Different Boiling Points, using Butanol

The apparatus consisted of a 500 ml flask equipped with magnetic stirring, addition funnel, and nitrogen inlet. The equipment was dried and inerted with nitrogen. To the flask was charged 150.0 g (0.5277 mol) of tetraisopropyl titanate. To the addition funnel was charged 103.0 g (1.0291 mol) of acetyl acetone. The system was inerted with nitrogen and stirring was started.

The acetyl acetone was added to the titanate (cooling may be applied if desired to remove reaction heat). After all of the acetyl acetone has been added, the mixture was stirred for 15 minutes.

The addition funnel was replaced with a vacuum distillation head. The liberated isopropyl alcohol was removed by vacuum distillation at 200 mbar (20 kPa), keeping the pot temperature below 70° C.

Vacuum was broken using nitrogen, and 43.7 g (0.5896 mol) of 1-butanol was added to the reaction mass. After stirring for 15 minutes at 60–70° C. vacuum was again applied and additional isopropyl alcohol was removed at 65–70° C. When the distillation was complete, the vacuum was further increased down to below 25 mbar (2.5 kPa) to reduce free alcohol concentrations below 1%.

High resolution $^1$H- and $^{13}$C-NMR showed that the final product contained 25 molar % of $Ti(C_5H_7O_2)_2(OC_4H_9)_2$, 50 molar % of $Ti(C_5H_7O_2)_2(OC_4H_9)(OC_3H_7)$, and 25 molar % of $Ti(C_5H_7O_2)_2(OC_3H_7)_2$. These ratios exclude free alcohol, which was found to be 0.3 weight % isopropyl alcohol and 0.2 weight % n-butyl alcohol. The overall ratio of bound isopropoxy to butoxy groups was 0.97 versus a target of 1.0.

Example 3

Different Boiling Points, using Tetrabutyl Titanate

The apparatus consisted of a 500 ml flask equipped with magnetic stirring, addition funnel, and nitrogen inlet. The equipment was dried and inerted with nitrogen. To the flask was charged 108.2 g (0.3807 mol) of tetraisopropyl titanate and 55.0 g (0.1629 mol) tetrabutyl titanate. To the addition funnel was charged 106.1 g (1.0602 mol) of acetyl acetone. The system was inerted with nitrogen and stirring was started.

The acetyl acetone was added to the titanate dropwise (cooling may be applied if desired to remove reaction heat). After all of the acetyl acetone was added, the mixture was stirred for 15 minutes.

The addition funnel was replaced with a vacuum distillation head. The liberated isopropyl and n-butyl alcohols were removed by vacuum distillation at 200 mbar (20 kPa), keeping the pot temperature below 70° C. The product obtained in this manner contained several percent residual free alcohol, which was reduced further by stripping at 70° C. and 5–15 mbar (0.5–15 kPa) pressure.

High resolution $^1$H- and $^{13}$C-NMR showed that the final product contained 25 molar % of $Ti(C_5H_7O_2)_2(OC_4H_9)_2$, 50 molar % of $Ti(C_5H_7O_2)_2(OC_4H_9)(OC_3H_7)$, and 25 molar % of $Ti(C_5H_7O_2)_2(OC_3H_7)_2$. These ratios exclude free alcohol, which was found to be 0.3 weight % isopropyl alcohol and 0.2 weight % n-butyl alcohol. The overall ratio of bound isopropoxy to butoxy groups was 1.0 versus a target of 1.0.

From the examples, a mixed titanium chelate containing about 23 to about 27% of $Ti(C_5H_7O_2)_2(OC_3H_7)_2$, about 48 to about 52% of $Ti(C_5H_7O_2)_2(OC_3H_7)(OC_2H_5)$, and about 23 to about 27% of $Ti(C_5H_7O_2)_2(OC_2H_5)_2$ cold be readily produced.

Comparative Example 1

Different Boiling Points, Using Tetrabutyl Titanate

The following shows the composition obtained using the process of U.S. Pat. No. 5,349,073.

Comp. Ex. 1A

Isopropyl Titanate Intermediate 1

The apparatus consisted of a 500 ml flask equipped with magnetic stirring, addition funnel, and nitrogen inlet. The equipment was dried and inerted with nitrogen. To the flask was charged 150.0 g (0.5277 mol) of tetraisopropyl titanate. To the addition funnel was charged 103.0 g (1.0291 mol) of acetyl acetone. The system was inerted with nitrogen and stirring started.

The acetyl acetone was added to the titanate dropwise (cooling may be applied if desired to remove reaction heat).

After all of the acetyl acetone has been added, the mixture was stirred for 15 minutes.

The addition funnel was replaced with a vacuum distillation head. The liberated isopropyl alcohol was removed by vacuum distillation at 200 mbar (20 kPa), keeping the pot temperature below 70° C. The intermediate obtained in this manner contained several percent residual free alcohol, which was reduced further by stripping at 70° C. and 15 mbar (1.5 kPa) pressure. This intermediate 1 was stored for later use.

Comp. Ex. 1B

Process Disclosed in U.S. Pat. No. 5,349,073
(Different Boiling Point Case)

The apparatus consisted of a 500 ml flask equipped with magnetic stirring, addition funnel, and nitrogen inlet. The equipment was dried and inerted with nitrogen. To the flask was charged 150.0 g (0.4407 mol) of tetrabutyl titanate. To the addition funnel was charged 86.0 g (0.8594 mol) of acetyl acetone. The system was inerted with nitrogen and stirring is started.

The acetyl acetone was added to the titanate dropwise (cooling may be applied if desired to remove reaction heat). After all of the acetyl acetone has been added, the mixture was stirred for 15 minutes.

The addition funnel was replaced with a vacuum distillation head. The liberated butyl alcohol was removed by vacuum distillation at 50 mbar (5 Pa), keeping the pot temperature below 70° C. The product obtained in this manner contained several percent residual free alcohol, which was reduced further by stripping at 70° C. and 15 mbar pressure. This intermediate product was left in the flask after the distillation was complete.

To the intermediate in the flask was added 159.6 g (0.4407 mol) of previously-prepared isopropyl titanate intermediate 1. The mixture was stirred for 1 hour at 60° C. under a slow nitrogen purge.

High resolution $^1$H- and $^{13}$C-NMR showed that the final product contained 26 molar % of $Ti(C_5H_7O_2)_2(OC_4H_9)_2$, 50 molar % of $Ti(C_5H_7O_2)_2(OC_4H_9)(OC_3H_7)$, and 24 molar % of $Ti(C_5H_7O_2)_2(OC_3H_7)_2$. These ratios exclude free alcohol, which was found to be 0.8 weight % isopropyl alcohol and 0.6 weight % n-butyl alcohol. The overall ratio of bound isopropoxy to butyl groups was 0.92 versus a target of 1.0. Significantly, this same acetylacetonate peak in the $^1$H-NMR spectrum of the di-isopropoxy chelate appears at 5.325 ppm, while that of the dibutoxy chelate appears at 5.335 ppm. The mixed alcohol chelate is found contain these same peaks, plus a new peak at 5.33 ppm. The product is thus confirmed to be a 1:2:1 mixture of the dibutoxy, isopropoxy-butoxy, and di-isopropoxy chelates.

What is claimed is:

1. A process comprising (1) contacting a tetraalkyl titanate with a chelating agent to produce a product mixture comprising a titanium chelate and an alcohol; (2) optionally substantially removing said alcohol to produce an alcohol-reduced titanium chelate; (3) contacting said product mixture or alcohol-reduced titanium chelate with a second alcohol to produce another alcohol-reduced titanium chelate; and optionally (4) reducing the alcohol content in said another alcohol-reduced titanium chelate to produce a substantially alcohol-free titanium chelate wherein said chelating agent is an organic 1,3-dicarbonyl compound and said second alcohol is less volatile than said alcohol.

2. A process according to claim 1 herein said chelating agent is selected from the group consisting of 2,4-pentanedione, 1,4-hexanedione, 1,3-pentanedione, 2,4-hexanedione, dipivaloylmethane, dimethyl malonate, diethyl malonate, methyl acetoacetate, ethyl acetoacetate, ethyl acetobutyrate, isopropyl acetoacetate, and combinations of two or more thereof.

3. A process according to claim 1 wherein said chelating agent is selected from the group consisting of 2,4-pentanedione, ethyl acetoacetate, or combinations thereof.

4. A process according to claim 1 wherein said tetraalkyl titanate is selected from the group consisting of tetraethyl titanate, tetrapropyl titanate, tetraisopropyl titanate, tetrabutyl titanate, tetraisobutyl titanate, tetra-tert-butyl titanate, tetrahexyl titanate, and combinations of two or more thereof.

5. A process according to claim 2 wherein said tetraalkyl titanate is selected from the group consisting of tetraethyl titanate, tetrapropyl titanate, tetraisopropyl titanate, tetrabutyl titanate, tetraisobutyl titanate, tetra-tert-butyl titanate, tetrahexyl titanate, and combinations of two or more thereof.

6. A process according to claim 5 wherein said alcohol is isopropanol and said second alcohol is butanol.

7. A process according to claim 6 wherein said tetraalkyl titanate is tetraisopropyl titanate.

8. A process according to claim 7 wherein said chelating agent is 2,4-pentanedione.

9. A process according to claim 8 wherein said process produces a titanium chelate comprising (A) $TiX_m(OR)_{4-m}$, (B) $TiX_m(OR)_{(4-m)/2}(OR^1)_{(4-m)/2}$, and (C) $TiX_m(OR^1)_{4-m}$; said substantially alcohol-free titanium chelate comprises 3.0% by weight or lower of said alcohol wherein X is a radical derived from a chelating agent comprising an organic 1,3-dicarbonyl compound; m is a number from about 1.5 to about 2.5; and R and $R^1$ are each independently a hydrocarbyl radical containing from 1 to about 10 carbon atoms per radical.

10. A process according to claim 9 wherein said substantially alcohol-free titanium chelate has an alcohol content of 2.0% by weight or lower.

11. A process according to claim 10 wherein said substantially alcohol-free titanium chelate is selected from the group consisting of
$Ti(CH_3C(O)CHC(O)CH_3)_{1.95}(OCH(CH_3)_2)_{2.05}$,
$Ti(CH_3C(O)CHC(O)CH_3)_{1.95}(OCH(CH_3)_2)_{1.025}(OCH_2CH_2CH_2CH_3)_{1.025}$,
$Ti(CH_3C(O)CHC(O)CH_3)_{1.95}(OCH_2CH_2CH_2CH_3)_{2.05}$;
$Ti(CH_3C(O)CHC(O)CH_3)_{1.95}(OCH(CH_3)_2)_{2.05}$,
$Ti(CH_3C(O)CHC(O)CH_3)_{1.95}(OCH(CH_3)_2)_{1.025}(OCH_2CH_3)_{1.025}$,
$Ti(CH_3C(O)CHC(O)CH_3)_{1.95}(OCH_2CH_3)_{2.05}$;
$Ti(OC(CH_3)CHC(O)CH_3)_{1.95}(OCH(CH_3)_2)_{2.05}$,
$Ti(OC(CH_3)CHC(O)CH_3)_{1.95}(OCH(CH_3)_2)_{1.025}(OCH_2CH_2CH_2CH_3)_{1.025}$,
$Ti(OC(CH_3)CHC(O)CH_3)_{1.95}(OCH_2CH_2CH_2CH_3)_{2.05}$;
$Ti(OC(CH_3)CHC(O)CH_3)_{1.95}(OCH(CH_3)_2)_{2.05}$,
$Ti(OC(CH_3)CHC(O)CH_3)_{1.95}(OCH(CH_3)_2)_{1.025}(OCH_2CH_3)_{1.025}$,
$Ti(OC(CH_3)CHC(O)CH_3)_{1.95}(OCH_2CH_3)_{2.05}$, and combinations of two or more thereof.

12. A process comprising (1) contacting a mixture comprising a tetraalkyl titanate and a second tetraalkyl titanate with a chelating agent to produce a product mixture comprising a titanium chelate and a mixture of alcohols derived from the tetraalkyl titanate and second tetraalkyl titanate; (2) substantially removing the mixture of alcohols to produce an alcohol reduced titanium chelate; and optionally (3) reducing the alcohol content of the alcohol-reduced titanium chelate to produce a substantially alcohol-free titanium chelate wherein said chelating agent is an organic 1,3- dicarbonyl compound and the alcohols derived from the tetraalkyl titanate and second tetraalkyl titanate have similar boiling points.

13. A process according to claim 12 wherein said chelating agent is selected from the group consisting of 2,4-pentanedione, ethyl acetoacetate, or combinations thereof.

14. A process according to claim 13 wherein said tetraalkyl titanate differs from said second tetraalkyl titanate and each of said tetraalkyl titanate and second tetraalkyl titanate is independently selected from the group consisting of tetraethyl titanate, tetrapropyl titanate, tetraisopropyl titanate, tetrabutyl titanate, tetraisobutyl titanate, tetra-tert-butyl titanate, tetrahexyl titanate, and combinations of two or more thereof.

15. A process according to claim 14 wherein each of said tetraalkyl titanate and second tetraalkyl titanate is independently selected from the group consisting of tetraethyl titanate, tetrapropyl titanate, tetraisopropyl titanate, tetrabutyl titanate, tetraisobutyl titanate, tetra-tert-butyl titanate, tetrahexyl titanate, and combinations of two or more thereof.

16. A process according to claim 15 wherein said tetraalkyl titanate is tetraisopropyl titanate and said second tetraalkyl titanate is tetraethyl titanate.

17. A process according to claim 16 wherein said chelating agent is 2,4-pentanedione.

18. A process according to claim 17 wherein said process produces a titanium chelate comprising (A) $TiX_m(OR)_{4-m}$, (B) $TiX_m(OR)_{(4-m)/2}(OR^1)_{(4-m)/2}$, and (C) $TiX_m(OR^1)_{4-m}$; said substantially alcohol-free titanium chelate comprises 3.0% by weight or lower of said alcohol wherein X is a radical derived from a chelating agent comprising an organic 1,3-dicarbonyl compound; m is a number from about 1.5 to about 2.5; and R and $R^1$ are each independently a hydrocarbyl radical containing from 1 to about 10 carbon atoms per radical.

19. A process according to claim 18 wherein said substantially alcohol-free titanium chelate has an alcohol content of 2.0% by weight or lower.

20. A process comprising contacting a compound of formula $TiX_m(OR)_{4-m}$ with an alcohol $R^1OH$ under a condition effective to produce a substantially alcohol-free titanium comprising (A) $TiX_m(OR)_{4-m}$, (B) $TiX_m(OR)_{(4-m)/2}(OR^1)_{(4-m)/2}$, and (C) $TiX_m(OR^1)_{4-m}$; said substantially alcohol-free titanium chelate comprises 3.0% by weight or lower of said alcohol wherein X is a radical derived from a chelating agent comprising an organic 1,3-dicarbonyl compound; m is a number from about 1.5 to about 2.5; and R and $R^1$ are each independently a hydrocarbyl radical containing from 1 to about 10 carbon atoms per radical.

21. A process comprising (1) contacting a mixture comprising a tetraalkyl titanate and a second tetraalkyl titanate with a chelating agent to produce a product mixture comprising a titanium chelate and a mixture of alcohol derived from said tetraalkyl titanate and alcohol derived from said second tetraalkyl titanate wherein said alcohol derived from said second tetraalkyl titanate is less volatile than said alcohol derived from said tetraalkyl titanate; (2) substantially removing said alcohol derived from said tetraalkyl titanate to produce an alcohol-reduced titanium chelate; (3) further reacting said alcohol-reduced titanium chelate with said alcohol derived from said second tetraalkyl titanate to produce a mixed titanium chelate; and optionally (3) reducing the alcohol content of said mixed titanium chelate to produce a substantially alcohol-free titanium chelate wherein said chelating agent is an organic 1,3-dicarbonyl compound.

\* \* \* \* \*